(12) United States Patent
Holaday

(10) Patent No.: US 9,107,878 B2
(45) Date of Patent: Aug. 18, 2015

(54) METHODS OF TREATING CANCER

(75) Inventor: John W. Holaday, Bethesda, MD (US)

(73) Assignee: EXOCYTE THERAPEUTICS PTE, LTD, Singapore (SG)

( * ) Notice: Subject to any disclaimer, the term of this patent is extended or adjusted under 35 U.S.C. 154(b) by 317 days.

(21) Appl. No.: 13/639,112

(22) PCT Filed: Apr. 6, 2011

(86) PCT No.: PCT/US2011/031359
§ 371 (c)(1),
(2), (4) Date: Jan. 8, 2013

(87) PCT Pub. No.: WO2011/127129
PCT Pub. Date: Oct. 13, 2011

(65) Prior Publication Data
US 2013/0202644 A1    Aug. 8, 2013

Related U.S. Application Data

(60) Provisional application No. 61/321,370, filed on Apr. 6, 2010.

(51) Int. Cl.
*A61K 35/14* (2015.01)
*A61K 39/00* (2006.01)
*A61K 35/15* (2015.01)
*A61K 35/13* (2015.01)

(52) U.S. Cl.
CPC ............... *A61K 35/15* (2013.01); *A61K 35/13* (2013.01); *A61K 39/0011* (2013.01); *A61K 2039/5154* (2013.01); *A61K 2039/5158* (2013.01)

(58) Field of Classification Search
None
See application file for complete search history.

(56) References Cited

U.S. PATENT DOCUMENTS

| | | | |
|---|---|---|---|
| 5,605,885 A | 2/1997 | Bernton et al. | |
| 8,338,173 B2 * | 12/2012 | Moser et al. | 435/347 |
| 2004/0028692 A1 | 2/2004 | Zitvogel et al. | |

FOREIGN PATENT DOCUMENTS

| | | |
|---|---|---|
| JP | 2000512161 A1 | 9/2000 |
| JP | 2011525191 A1 | 9/2011 |
| WO | WO2007049737 A1 | 3/2007 |
| WO | WO2004071518 A1 | 8/2014 |

OTHER PUBLICATIONS

Morelli et al (Blood, 2004, vol. 104, pp. 3257-3266).*
Valadi et al, Nature Cell Biology, 2007, vol. 9, p. 654-659.*
International Search Report and Written Opinion dated Jul. 26, 2011 for PCT/US11/31359, pp. 1-9.
Andre, F. et al., "Exosomes for Cancer Immunotherapy," Annal Oncol., 2004, vol. 15, Suppl. 4, pp. iv141-4.
Kashanchi, F. et al., "Electroporation of Viral Transactivator Proteins into Lymphocyte Suspension Cells," Nucleic Acids Res., Sep. 11, 1992, vol. 20, No. 17, pp. 4673-4674.
Li et al., "Delivery of Exogenous Antigen into the Major Histocompatibility Complex Calss I and Class II Pathways by Electroporation," J Leukoc Biol., Nov. 1994, vol. 56, No. 5, pp. 616-624.
Lohmann, S. et al., CD83+ Human Dendritic Cells Transfected with Tumor Peptide cDNA by Electroporation Induce Specific T-Cell Responses: A Potential Tool for Gene Immunotherapy, Cancer Gene Ther., Apr. 2000, vol. 7, No. 4, pp. 605-614.
Chen, et al., "Effect of CTL on K562 Cell Induced by Exosomes and in Combination with CPG OND", Journal of Experimental Hematology, vol. 16, No. 2, 2008, 272-275.
Huang, et al., "Exosomes", Guangxi Yike Daxue Xuebao, vol. 26, No. 5, 2009, 715-717.
Ilett, et al., "Dendritic Cell Activation by Tumor Cell-Derived Exosomes", Clinical Immunology, vol. 119, Supplement, 2006, S149-150.
Lohmann, et al., "CD83 Human Dendritic Cells Transfected with Tumor Peptide cDNA by Electroporation Induce Specific T-Cell Responses: A Potential Tool for Gene Immunotherapy", Cancer Gene Ther., vol. 7, No. 4, 2000, 605-614.
Zitvogel, et al., European Journal of Cancer, vol. 35, Supl., 1999, S128.

* cited by examiner

Primary Examiner — Karen Canella
(74) Attorney, Agent, or Firm — Ian J. Griswold; Johnson, Marcou & Isaacs, LLC

(57) ABSTRACT

The present invention relates to compositions and methods for treating an animal with a tumor or other metabolic disorder. In particular, the presently disclosed subject matter relates to methods of electroporating exosomes shed by tumors and by other metabolic disorders into immune cells such as dendritic cells and T cells. Administration of the electroporated immune cells to an animal with a tumor results in an increased immune response to the tumor and treatment of the tumor.

19 Claims, No Drawings

METHODS OF TREATING CANCER

CROSS-REFERENCE TO RELATED APPLICATIONS

This application is the 35 U.S.C. 371 national phase patent application of International Patent Application Number PCT/US2011/031359, filed on Apr. 6, 2011, published in English and designating the U.S., and claims the benefit of U.S. Provisional Patent Application No. 61/321,370, filed Apr. 6, 2010, the disclosure of which is incorporated herein by reference in its entirety.

FIELD OF THE INVENTION

The present invention relates to compositions and methods for treating an animal with a tumor or other metabolic disorder. In particular, the presently disclosed subject matter relates to methods of isolating and purifying exosomes shed by tumors and by other metabolic disorders. Then using electroporation to insert the proteins and nucleotide sequences encoding the one or more proteins or polypeptides from the exosomes into antigen-presenting cells, such as dendritic cells, or other immune cells, such as T cells, and administering the antigen-presenting cells or other immune cells to the animal to increase an immune response.

BACKGROUND OF THE INVENTION

Cancer is a class of disease caused by a failure of the controls that normally govern cell proliferation, differentiation and cell survival. Cells that undergo malignant transformation escape normal growth controls, invade surrounding tissue and may ultimately migrate to other sites in the body to establish secondary tumors. Cancer therapy typically involves surgery (for solid tumors) followed by cytotoxic drugs or radiation, either alone or in combination, to kill the cancer cells. An ongoing quest in detecting and treating cancer has been to find ways of educating the body's immune system to mount an orchestrated effort to kill cancer cells by activating the humoral and cellular immune systems to specifically attack growing cancer cells and spare the normal cells necessary for life.

One proposed method to treat cancer is to educate antigen-presenting cells, such as dendritic cells. Dendritic cells are immune cells that form part of an animal's immune system. Their main function is to process antigen material and present it on the surface to other cells of the immune system, thus functioning as antigen-presenting cells. They act as messengers between the innate and adaptive immunity. Dendritic cells are present in small quantities in an immature state in the blood. Once activated, they migrate to the lymphoid tissues where they interact with T and B lymphocytes to initiate and shape the adaptive immune response. Dendritic cells can be isolated and purified from animals.

Another proposed method to treat cancer is to directly educate T lymphocytes, part of the immune response necessary for activation of cellular immunity.

One strategy to treat cancer has been to insert the genetic contents of growing malignant tumors into the dendritic cells using flow electroporation. One application for flow electroporation is to use this technology to take malignant cells, removed from growing tumors in patients, and inserting them (or their lysed contents) into dendritic cells. This results in the education of dendritic cells such that when they are returned to the donor, both cellular and humoral immune responses are mounted to attack the malignant cells. A limitation of this process is the availability of malignant cells to electroporate into the dendritic cells of the donor. This requires a biopsy of the cancerous tissue, with inherent problems of surgery for biopsy, the inability to ensure that the biopsy contains relevant malignant tissue samples, and many types of cancers are not amenable to biopsy.

Previous studies have shown that cancer cells shed small packages of genetic information from growing tumors, called exosomes. Exosomes secreted by cells under normal and pathological conditions contain proteins, DNA and functional RNA molecules including mRNA and miRNA, which can be shuttled from one cell to another, affecting the recipient cell's protein production. Tumor exosomes are distinct from exosomes shed by normal cells. They are more abundant in cancer patients and they have an important role in the increased tumor growth, angiogenesis and the escape from the immune-surveillance. (Nilsson et al., Br J Cancer (2009) 100: 1603-1607). Genetic material and proteins contained within exosomes are the biological fingerprints of their malignant source cells.

Thus, there exists a need in the art for novel compositions and methods of use to treat cancer by directing the animal's own immune system to the cancer cells.

SUMMARY OF THE INVENTION

This invention is directed to methods to isolate and purify the exosomes shed by tumors and by other metabolic disorders, then to use electroporation to insert the exosome material into dendritic cells, T lymphocytes or other relevant immune cells. This milieu of genetic and protein information will be processed by dendritic cells, T lymphocytes or other relevant immune cells, enabling them to mount both cellular and humoral responses to malignant diseases, as well as metabolic disorders. It is recognized that the activated immune system will attack and disable the errant cells and enable a return to homeostasis and health.

DETAILED DESCRIPTION OF THE INVENTION

The present invention is related to methods and compositions useful for treating proliferative disorders such as, but not limited to, a cancer and/or a tumor. More particularly, the present invention includes methods of treating a tumor in an animal, comprising administering to the animal an effective amount of a composition comprising one or more antigen presenting cells, wherein the one or more antigen presenting cells are electroporated with one or more exosomes derived from the tumor (hereinafter "tumor exosomes"). In a preferred embodiment, the antigen-presenting cell is a dendritic cell.

Another preferred embodiment includes methods of treating a tumor in an animal by administering an effective amount of a composition comprising one or more T lymphocytes, wherein the one or more T lymphocytes are electroporated with one or more exosomes derived from the tumor. T lymphocytes or "T cells" are a group of white blood cells that function in cell-mediated immunity. Cell-mediated immunity or a "cell-mediated immune response" refers to the immunological defense provided by lymphocytes, such as T lymphocytes, when they come into close proximity to their target cells. A cell-mediated immune response also comprises lymphocyte activation in response to a specific antigen.

As used herein and in the appended claims, the singular forms "a", "an", and "the" include plural reference unless the context clearly indicates otherwise. Thus, for example, reference to a "compound" is a reference to one or more such compounds and includes equivalents thereof known to those skilled in the art, and so forth.

The term "animal" includes a human, and more particularly, a mammal.

As used herein, "antigen-presenting cell" or "APC" means a cell capable of handling and presenting antigen to a lymphocyte or another immune effector cell. Examples of antigen-presenting cells include, but are not limited to, macrophages, Langerhans-dendritic cells, follicular dendritic cells, B cells, monocytes, fibroblasts and fibrocytes. As used herein, "modified" to present an epitope refers to antigen-presenting cells that have been manipulated to present an epitope by natural or recombinant methods. For example, the antigen-presenting cells can be modified by electroporating the antigen-presenting cell with at least one tumor exosome to modify the antigen-presenting cell to express a tumor polypeptide.

The term "treating", "treat" or "to treat" as used herein means the prevention, reduction, partial or complete alleviation or cure of a disease or a tumor. Treating cancer as used herein may include reducing the proliferation of, de-differentiation of, or spread of cancerous cells or combinations thereof. This includes cancers of different tissues, and cancers at different stages including, but not limited to, leukemia, brain cancer, prostate cancer, liver cancer, ovarian cancer, stomach cancer, colorectal cancer, throat cancer, breast cancer, skin cancer, melanoma, lung cancer, sarcoma, cervical cancer, testicular cancer, bladder cancer, endocrine cancer, endometrial cancer, esophageal cancer, glioma, lymphoma, neuroblastoma, osteosarcoma, pancreatic cancer, pituitary cancer, renal cancer, nasopharyngeal cancer and the like. Treating a tumor according to the present invention includes a reduction in tumor size, a reduction in tumor growth, and a reduction in tumor metastasis. As used herein, the term "tumor" refers to abnormal tissue masses, and includes both benign and malignant masses.

The term "tumor exosome" refers to an exosome containing tumor polypeptides, tumor DNA and/or tumor RNA, and includes exosomes derived from particular types of cancers, including, but not limited to prostasomes. An exosome is created intracellularly when a segment of the cell membrane spontaneously invaginates and is endocytosed. The internalized segment is broken into smaller vesicles that are subsequently expelled from the cell. The latter stage occurs when the late endosome, containing many small vesicles, fuses with the cell membrane, triggering the release of the vesicles from the cell. The vesicles (once released are called "exosomes") consist of a lipid raft embedded with ligands, i.e., polypeptides, common to the original cell membrane. Exosomes secreted by cells under normal and pathological conditions contain proteins, DNA and functional RNA molecules, including mRNA and miRNA, which can be shuttled from one cell to another, affecting the recipient cell's protein production. This RNA is called "exosomal shuttle RNA" or "exosome RNA".

Exosomes may be obtained from a biological sample or a tissue sample from an animal. In preferred embodiments, tumor exosomes are isolated from a biological sample, including, but not limited to, a blood sample, a urine sample, and a tumor ascites sample. Exosomes may be isolated from the animal sample by centrifugational techniques, ultrafiltration techniques, or affinity chromatography techniques that recognize the proteins (e.g. EGF receptor, ICAM-1, VEGF or LMP1 (Epstein Barr Virus Latent Membrane Protein 1)) expressed on the surface of exosomes. Affinity chromatography techniques may also employ antibodies or other materials that bind to a previously identified exosome biomarker that is shown to be located on the exterior of the exosome. A list of exosome biomarkers can be found in the following references: Nilsson et al, British Journal of Cancer 100(10):1603-7 (2009); and Skog et al., Nature Cell Biology 10(12) 1-7 (2008). Exosomes may be purified by using methods that are known in the art, for example those methods taught by U.S. patent application Ser. No. 12/695,910, Gastpar et al. Cancer Research, 65(12):5238-5248, Simpson et al., Expert Review Proteomics 6(3):267-283 (2009) Caby et al., Exosomal-like vesicles are present in human blood plasma, Int. Immunol. 17(7) 879-887 (2005). This and all documents referred to in this specification are herein incorporated by reference in their entirety.

In one embodiment, exosomes released by, or exocytosed from cancer cells are transfected into antigen-presenting cells such as dendritic cells. Any transfection methods may be used to insert the exosome, or the contents of the exosome into the antigen-presenting cell. In one embodiment, electroporation is the transfection method that is used to insert the exosome, or the contents of the exosome into the antigen-presenting cell. Any antigen-presenting cell is contemplated for use in the present methods, and may be an autologous cell or an allogeneic cell. Those of skill in the art are familiar with methods of electroporation. The electroporation may be, for example, flow electroporation or static electroporation. Accordingly, the term "transfected" as used herein encompasses being electroporated. Electroporation of tumor exosomes into antigen-presenting cells such as dendritic cells (or T lymphocytes as later described) results in the priming of these cells in a tumor specific manner, and possibly a tumor metastasis specific manner. Use of tumor exosomes for priming dendritic cells, T lymphocytes or other immune cells provides an advantage over other methods of priming these cells because the tumor exosome serves as a pre-concentrated packet of tumor RNA and tumor proteins that are involved in the metastasis of cancers and/or tumors. Thus, the cells electroporated with the tumor exosomes should present, or be activated to recognize, higher amounts of those antigens/proteins that are involved in the spread and/or proliferation of the cancer or tumor, resulting in an increased immune response against these very antigens/proteins and a more successful treatment of the cancer or tumor.

In one embodiment, the method of electroporating the antigen-presenting cells comprises use of an electroporation device as described in U.S. patent publication 20030073238, or Van Meirvenne et al., Cancer Gene Therapy 9:787-797 (2002) both of which are incorporated herein by reference. Methods and devices for electroporation are also described in, for example, published PCT Application Nos. WO 03/018751 and WO 2004/031353; U.S. patent application Ser. Nos. 10/781,440, 10/080,272, and 10/675,592; and U.S. Pat. Nos. 5,720,921, 6,074,605, 6,090,617, 6,773,669, 6,090, 617, 6,485,961, 6,617,154, 5,612,207, all of which are incorporated by reference. Another apparatus for use in flow electroporation is described in U.S. Patent Publication 20080138877 and U.S. Pat. No. 6,773,669 which are incorporated by reference herein in their entirety.

It should be understood that the term "tumor exosome" includes both intact tumor exosomes and fragmented tumor exosomes. In this regard, the term "intact" includes, but is not limited to, exosomes that are whole, complete or undamaged. The term "fragmented" includes, but is not limited to, exosomes that are broken, divided, or dissociated. It is possible that electroporation itself disrupts the exosome and results in a fragmented exosome. As used herein, a "tumor exosome lysate" includes a fragmented exosome and materials inside the tumor exosome prior to fragmentation. Materials inside the tumor exosome include tumor RNA, tumor DNA and tumor proteins. It should be understood that, as used herein, the term "tumor RNA" refers to RNA derived from a tumor exosome. As also used herein, the term "tumor DNA" refers to DNA derived from a tumor exosome and the term "tumor protein" refers to protein or peptide derived from a tumor exosome.

Accordingly, the present invention includes electroporation of an entire exosome into an antigen-presenting cell, T lymphocyte or other immune cell, electroporation of fragments of an exosome into an antigen-presenting cell, T lymphocyte or other immune cell, electroporation of a tumor exosome lysate into an antigen-presenting cell, T lymphocyte or other immune cell, and electroporation of amplified tumor RNA and/or amplified tumor DNA into an antigen-presenting cell, T lymphocyte or other immune cell. In some embodiments, RNA from the tumor exosome lysate is isolated, reverse transcribed and amplified prior to re-combining with the tumor exosome lysate to create a tumor lysate/tumor DNA mixture. The tumor lysate/tumor DNA mixture is then electroporated into the dendritic cell, T cell or other immune cell. In other embodiments, RNA from the tumor exosome lysate is isolated, reverse transcribed, amplified, and translated into tumor protein prior to electroporation. In these embodiments, the tumor protein is re-combined with the tumor exosome lysate to create a tumor lysate/tumor protein mixture which mixture is electroporated into the dendritic cell, T cell or other immune cell.

Accordingly, the present invention includes a method of treating an animal with a tumor, comprising, administering to the animal an effective amount of a composition comprising one or more antigen-presenting cells, wherein the one or more antigen-presenting cells are electroporated with one or more tumor exosomes or tumor exosome lysates. In preferred embodiments, the electroporated antigen-presenting cell comprises tumor RNA, tumor DNA, tumor protein, or any combination thereof following electroporation. In further preferred embodiment, the antigen-presenting cells and the tumor exosomes or tumor exosome lysates are derived from the animal to be treated.

The present invention further includes a method of treating an animal with a tumor, comprising: administering to the animal an effective amount of a composition comprising one or more T lymphocytes, wherein the one or more T lymphoyctes are electroporated with one or more tumor exosomes or tumor exosome lysates. In preferred embodiments, the electroporated T lymphocyte comprises tumor RNA, tumor DNA, tumor protein, or any combination thereof following electroporation. In further preferred embodiment, the T lymphocytes and the tumor exosomes or tumor exosome lysates are derived from the animal to be treated.

Methods are also provided herein where a tumor is treated in an animal by administering to the animal an effective amount of a composition comprising one or more T lymphocytes, wherein the one or more T lymphocytes are electroporated with one or more tumor exosomes comprising tumor RNA that encodes a tumor polypeptide. "Tumor polypeptide" is defined in more detail below. In a preferred embodiment, the tumor polypeptide is believed to be, or is shown to be, associated with the tumor in the animal. The present invention further includes methods of treating a tumor in an animal, comprising administering to the animal an effective amount of a composition comprising one or more antigen presenting cells, wherein the one or more antigen presenting cells are electroporated with one or more tumor exosomes comprising tumor RNA that encodes a tumor polypeptide. In a preferred embodiment, the tumor polypeptide is believed to be, or is shown to be, associated with the tumor in the animal.

In certain embodiments, dendritic cells or "DCs" are a preferred type of antigen-presenting cell. The dendritic cells are modified, transformed or altered in such a way that they present epitopes that direct an immune response to the cells from which the inserted exosomes were obtained. Accordingly, the present invention further includes methods of treating a tumor in an animal, comprising administering to the animal an effective amount of a composition comprising one or more dendritic cells, wherein the one or more dendritic cells are electroporated with one or more tumor exosomes or tumor exosome lysates.

Dendritic cells function to process antigen material and present the antigen material on the surface to other cells of the immune system. Dendritic cells may also be obtained by inducing progenitor cells to become dendritic cells. Dendritic cells are found in many non-lymphoid tissues, but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells. Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid.

Dendritic cells are conveniently categorized as "immature" and "mature" cells, which allow a simple way to discriminate between two well-characterized phenotypes. However, this nomenclature should not be construed to exclude all possible intermediate stages of differentiation. Immature dendritic cells are characterized as antigen-presenting cells with a high capacity for antigen uptake and processing, which correlates with the high expression of Fcγ receptor, mannose receptor and DEC-205 marker. "Immature dendritic cell" also refers to a dendritic cell that has not matured to a state where they are capable of eliciting a T or B cell response. Once a dendritic cell comes into contact with a presentable antigen, it becomes activated into a "mature dendritic cell."

In one embodiment, mature dendritic cells are electroporated with exosomes. This preferred embodiment bypasses the inherent antigen uptake limits of mature dendritic cells. Mature dendritic cells are typically characterized by a lower expression of the Fcγ receptor, mannose receptor and DEC-205 marker, but a high expression of cell surface molecules responsible for T cell activation such as class I and class II NMC, adhesion molecules (e.g., CD54 and CD11) and co-stimulatory molecules (e.g., CD40, CD80 and CD86). They are characterized as efficient at antigen presentation. Dendritic cells may be differentiated ex vivo by adding a combination of cytokines such as GM-CSF, IL-4, IL-13 and/or TNFa to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFa, CD40 ligand, LPS, flt3 ligand and/or other compound(s) that induce maturation and proliferation of dendritic cells.

Accordingly, as used herein, the term "dendritic cell" includes, but is not limited to, a Langerhans-dendritic cell, an interstitial dendritic cell, a follicular dendritic cell, an afferent lymph veiled dendritic cell, a blood dendritic cell, a lymphoid dendritic cell, an interdigitating dendritic cell, a mature dendritic cell, and an immature dendritic cell.

In preferred embodiments, the dendritic cell is isolated from the animal receiving a treatment or administration as described herein. The present invention encompasses methods of treating tumors in an animal and methods of increasing immune responses in animal wherein one or more immature dendritic cells are isolated from the animal, and then the one or more immature dendritic cells are 1) electroporated with one or more tumor exosomes or tumor exosome lysates, 2) matured in vitro, and 3) administered to the animal. The present invention further encompasses methods of treating tumors in an animal and methods of increasing immune responses in animal wherein one or more immature dendritic cells are isolated from the animal, and then the one or more immature dendritic cells are 1) electroporated with one or more tumor exosomes or tumor exosome lysates and 2) administered to the animal. In these embodiments, the dendritic cells may be administered to the animal in a particular location for maturation in vivo. (See U.S. Pat. No. 7,785,583, which is incorporated by reference herein in its entirety.) The present invention still further encompasses methods of treating tumors in an animal and methods of increasing immune responses in animal wherein one or more mature dendritic cells are isolated from the animal, the dendritic cells are 1) matured in vitro, 2) electroporated with one or more tumor exosomes or tumor exosome lysates and 3) administered to the animal. The present invention still further encompasses methods of treating tumors in an animal and methods of increasing immune responses in animal wherein one or more mature dendritic cells are isolated from the animal, and then the one or more dendritic cells are 1) electroporated with one or more tumor exosomes or tumor exosome lysates and 2) administered to the animal.

In certain embodiments, the present invention provides methods and compositions for eliciting an immune response to a tumor in an animal. For example, antigen-presenting cells electroporated with one or more tumor exosomes may be administered to an animal as an immunostimulatory composition or cellular vaccine. In particular embodiments, antigen-presenting cells electroporated with one or more tumor exosomes obtained from cancer cells are administered to the animal as an immunostimulatory composition or vaccine.

In certain embodiments, the present invention provides methods and compositions directed to increasing an immune response to the cells of the above-described cancers and/or tumors. In preferred embodiments, increasing an immune response to a tumor or cancer in an animal is achieved by increasing an immune response to a tumor or cancer polypeptide in the animal. Accordingly, the present invention provides a method of increasing an immune response to a tumor in an animal comprising: administering to the animal an effective amount of a composition comprising one or more electroporated antigen-presenting cells, or one or more electroporated T lymphocytes, wherein the one or more electroporated antigen-presenting cells or T lymphocytes are electroporated with one or more tumor exosomes or tumor exosome lysates. In preferred embodiments, the electroporated antigen-presenting cell or T lymphocyte comprises tumor RNA, tumor DNA, tumor protein, or any combination thereof, following electroporation. In further preferred embodiments, the antigen-presenting cells or T lymphocytes and the tumor exosomes or tumor exosome lysates are derived from the animal to be treated.

In other or further preferred embodiments, the antigen-presenting cell is a dendritic cell. Accordingly, the present invention provides a method of increasing an immune response to a tumor in an animal comprising: administering to the animal an effective amount of a composition comprising one or more electroporated dendritic cells, wherein the one or more electroporated dendritic cells are electroporated with one or more tumor exosomes or tumor exosome lysates. In preferred embodiments, the electroporated dendritic cell comprises tumor RNA following electroporation. In further preferred embodiment, the dendritic cells and the tumor exosomes or tumor exosome lysates are derived from the animal to be treated.

In other embodiments, a method of increasing an immune response to one or more tumor polypeptides in an animal is provided that comprises administering to the animal an effective amount of a composition comprising one or more electroporated antigen-presenting cells, wherein the one or more electroporated antigen-presenting cells are electroporated with one or more tumor exosomes or tumor exosome lysates. In preferred embodiments, the electroporated antigen-presenting cell is a dendritic cell and comprises tumor RNA following electroporation. In further preferred embodiments, the dendritic cells and the tumor exosomes or tumor exosome lysates are derived from the animal to be treated. In still further preferred embodiments, the tumor polypeptide is believed to be, or is shown to be, derived from a tumor in the animal.

As used herein, an "immune response" is defined as a bodily defense reaction that recognizes an antigen, which reaction may be achieved via the action or activation of any immune effector cell, or any combination thereof, including, but not limited to, a B cell, a T cell, a natural killer cell (NK cell), a dendritic cell, a macrophage, a monocyte, a granulocyte, a neutrophil, an eosinophil, and a basophil. The term "antigen" refers to a peptide or lipid derived from a substance, including, but not limited to, a virus, fungus, bacterium, pathogen, tumor, and self-reactive cell, that induces an immune response. As used herein, the term "polypeptide" refers to any polymer of amino acids, or amino acid analogs, regardless of size and function.

Increasing an immune response to a tumor polypeptide includes recognition or presentation of any portion or fragment of the tumor polypeptide by an immune effector cell. The portion of the tumor polypeptide so recognized may be a contiguous or non-contiguous span of amino acids. As used herein, the term "tumor polypeptide" refers to any polypeptide that is associated with the presence of a tumor or with tumor growth, including any polypeptide expressed by a tumor cell in an increased amount as compared to a non-tumor cell. In some embodiments, a tumor polypeptide is expressed in a tumor cell, but is not expressed in a non-tumor cell. Researchers have reported that the exosomes from cancer patients contain biomarkers for cancer that are useful for diagnostic purposes. (See Nilsson et al, British Journal of Cancer 100(10):1603-7 (2009); and Skog et al., Nature Cell Biology 10(12) 1-7 (2008) which are herein incorporated by reference in their entirety). Accordingly, the term "tumor polypeptide" includes all such exosome biomarkers previously elucidated.

As used herein, "activation" or "activating" refers to the stimulation of a B cell, T cell, or any immune effector cell, to proliferate and/or differentiate. Thus, for example, an "activated B cell" refers to a B cell that has been signaled to proliferate and/or differentiate. Also, for example, an "activated T cell" refers to a T cell that has been signaled to proliferate and/or differentiate. This is in contrast to a naive B cell, which is typically quiescent. Those of skill in the art will be familiar with methods of identifying an activated B cell. One method is to simply observe the proliferation of the activated B cells. Other approaches include assessing the expression of one or more molecules, such as co-stimulatory molecules (e.g., CD80, CD86) or adhesion molecules (e.g., ICAM-I), that are up-regulated in activated B cells. Similar analysis of other effector cells can be made to determination their activation via the methods of the present invention.

In certain aspects of the invention, the population of B cells is obtained from an animal. The cells may be obtained by any method known in the art. In a preferred embodiment, the cells are obtained from the peripheral blood of the subject. In certain embodiments, the subject has leukemia.

Combination Treatment

In some embodiments, it may be desirable to combine treatment using these transfected cancer and/or tumor cells with other agents or methods effective in the treatment of cancer. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the transfected cancer cells and the other includes the second agent(s).

Tumor cell resistance to chemotherapy and radiotherapy agents represents a major problem in clinical oncology. One goal of current cancer research is to find ways to improve the efficacy of chemotherapy and radiotherapy by combining it with immunotherapy. In the context of the present invention, it is contemplated that the electroporated dendritic cells could be used similarly in conjunction with chemotherapeutic, radiotherapeutic, or other immunotherapeutic intervention.

1. Chemotherapy

Cancer therapies include a variety of combination therapies with both chemical and radiation based treatments. One of ordinary skill in the art would be familiar with the range of chemotherapeutic agents and combinations that are available. Chemotherapeutic agents include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

2. Radiotherapy

Other factors that cause DNA damage and have been used extensively include gamma-rays, X-rays, and the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

The electroporated dendritic cells of the present invention may be administered in combination with other forms of immunotherapy. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The electroporated dendritic cells of the present invention may also be administered in combination with lymphocyte stimulators including, but not limited to, a prolactin agonist or a dopamine antagonist that stimulates endogenous prolactin release as described in U.S. Pat. No. 5,605,885, which is incorporated by reference herein in its entirety.

EXAMPLES

Example 1

Purification of Exosomes from a Biologic Sample

Samples are obtained after informed consent from a cancer cell sample from the animal such as tumor biopsy, or a sample of a biological fluid from the animal such as blood, urine, lymph, or saliva. The microvesicular fraction is prepared by differential centrifugation. First, cells are pelleted at 500 g for 20 min at 10 C and discarded, and then additional cellular debris is removed by centrifugation at 16 000 g for 20 min at 10 C, followed by filtration through a 0.45 mm filter device (Millipore). The microvesicles in the filtrate are then pelleted by ultracentrifugation (Beckman Ti70 rotor) at 100,000 g for 90 minutes at 10 C. For electron microscopic studies, the microvesicles are additionally purified by ultracentrifugation in a 20 and 40% sucrose gradient and then washed with filtered phosphate-buffered saline (PBS).

Tumor-specific exosomes, or tumor exosomes, are isolated from the microvesicular pellet using affinity chromatography techniques that recognize the proteins (e.g. EGF receptor, ICAM-1, VEGF, MAGE-1, and/or LMP1 (Epstein Barr Virus Latent Membrane Protein 1)) expressed on the surface of the exosomes.

Example 2

Purification of Tumor Cell Exosomes and Transfection of Dendritic Cells

Cancer cells at passage 1-15 are cultured in microvesicle-free medium (DMEM containing 5% dFBS) and conditioned medium from 4×10⁷ cells is collected after 48 hours. Microvesicles are purified by differential centrifugation. In brief, cancer cell-conditioned medium is centrifuged for 10 minutes at 300 g to eliminate cell contamination. Supernatants are further centrifuged for 20 minutes at 16,500 g and filtered through a 0.22 µm filter. Microvesicles are pelleted by ultracentrifugation at 110,000 g for 70 minutes. The microvesicle pellets are washed in 13 ml PBS, pelleted again and resuspended in PBS. Microsomes are measured for their protein content using the DC protein assay (Bio-Rad). Serum microsomes from healthy controls and cancer patients are diluted to 13 ml in PBS and sterile-filtered before centrifugation.

Bone marrow-derived dendritic cells are generated following the protocol described by Lutz et al. Briefly, bone marrow cells are isolated from the hind limbs and treated with red blood cell lysis buffer. The cells are plated in a 10-cm bacteriological Petri dish (Falcon-Becton Dickinson, Erembodegem, Belgium) at 2×10⁶ cells in 10 mL of complete medium (DMEM supplemented with 5% heat—inactivated FCS, 2 mM glutamine, 50 M 2-ME, 100 U/mL penicillin, 100 g/mL streptomycin, and 20 ng/mL rmo GM-CSF). On day 3 of culture, 10 mL of culture medium containing 20 ng/mL rmo GM-CSF is added. On day 5, 50% of the medium is refreshed with culture medium containing 20 ng/mL rmo GM-CSF. On day 7, cells are used for mRNA electroporation and according to the experimental set-up dendritic cells are further matured with LPS derived from *Escherichia coli* serotype O55:B5 (Sigma-Aldrich, Bornem, Belgium) at a concentration of 0.1 g/mL.

Dendritic cells can also be made by stimulating other immune cells to differentiate or de-differentiate.

Immediately before transfection, dendritic cells are washed twice in PBS (Invitrogen-Life Technologies) and collected by centrifugation for 10 minutes at 1500 rpm. The cells are re-suspended in Opti-MEM (Invitrogen-Life Technologies) to a final concentration of 20×10⁶ cells/mL. Subsequently, 200 L of the cell suspension is mixed with 20 g of mRNA in a 0.4-cm gap sterile disposable electroporation cuvette and electroporated with an Easyject Plus apparatus (Equibio, Kent, UK). Cells are transfected with a voltage pulse of 300 V in combination with a capacitance of 150 F and a pulse time of 6 milliseconds. After electroporation, cells are immediately re-suspended in fresh complete medium and further incubated at 37° C. in a humidified atmosphere supplemented with 7% $CO_2$.

Example 3

Flow Electroporation of Dendritic Cells

Exosomes obtained from cancer cells or biological fluids from an animal with cancer are incorporated into a patient's autologous cells by a flow electroporation system such as the one described in U.S. Patent Publication 20030059945, which is incorporated by reference herein in its entirety.

Dendritic cells are harvested from an animal. Either immature or mature dendritic cells may be harvested. If immature dendritic cells are harvested, the dendritic cells may be matured either before or after electroporation. For electroporation, the dendritic cells are resuspended in B&K pulsing buffer (125 mM KCl, 15 mM NaCl, 1.2 mM $MgCl_2$, 25 mM Hepes, 3 mM Glucose, pH 7.4) and transfected with pTM7 (100 ug/mL) using a flow electroporation system such as the one described in U.S. Patent Publication 20030059945 at the following pulse parameters: 2.1 KV/cm, 400 ms, 4 pulses at a 1.25 second interval, and flowing at 0.1 mL/s. Then the dendritic cells are incubated in the pulsing medium for 20 minutes before returning cells to the donor animal. Previous studies using this flow electroporation system have shown that about 75% of the cell population may be transfected.

Example 4

Administration of Dendritic Cells to an Animal

Dendritic cells that have been electroporated according to the methods of Example 3 are either matured in vitro and subsequently administered to the animal to be treated or administered to the animal directly following electroporation. When the dendritic cells are administered without prior in vitro maturation, the methods for in situ maturation, including administration routes, as described in U.S. Pat. No. 7,785,583 may be employed.

Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention, which are obvious to those skilled in the art, are intended to be covered by the present invention.

What is claimed is:

1. A method of treating an animal with a tumor comprising:
    electroporating one or more dendritic cells with:
        one or more tumor exosomes,
        one or more tumor exosome lysates,
        amplified tumor RNA obtained from one or more tumor exosome lysates,
        amplified tumor DNA obtained from one or more tumor exosome lysates,
        tumor proteins isolated from the one or more tumor exosome lysates,
        or any combination thereof, and
    administering to the animal an effective amount of a composition comprising the one or more electroporated dendritic cells.

2. The method of claim 1, wherein the one or more dendritic cells are isolated from the animal.

3. The method of claim 1, wherein the one or more tumor exosomes are isolated from a biological sample of the animal.

4. The method of claim 3, wherein the biological sample is a blood sample, a urine sample or tumor ascites sample.

5. The method of claim 1, wherein the animal is a human.

6. The method of claim 1 wherein the amplified DNA is obtained by
    isolating tumor RNA from the one or more tumor exosome lysates,
    reverse transcribing the isolated tumor RNA to DNA, and amplifying the DNA.

7. The method of claim 1 wherein the amplified DNA is obtained by
    isolating tumor DNA from the one or more tumor exosome lysates, and amplifying the tumor DNA.

8. The method of claim 1, further comprising administering to the animal an effective amount of a prolactin agonist or a dopamine antagonist.

9. A method of increasing an immune response to one or more tumor polypeptides in an animal comprising:
    electroporating one or more dendritic cells with tumor exosomes comprising RNA encoding the one or more tumor polypeptides, administering to the animal an effective amount of a composition comprising the one or more dendritic cells.

10. The method of claim 9, wherein the one or more dendritic cells are isolated from the animal.

11. The method of claim 9, wherein the tumor exosomes are isolated from a blood, urine or ascites sample of the animal.

12. The method of claim 9, wherein the tumor exosomes are intact.

13. A method of increasing an immune response to one or more tumor polypeptides in an animal comprising:
   administering to the animal an effective amount of a composition comprising one or more dendritic cells, wherein the one or more dendritic cells are electroporated with tumor exosomes comprising RNA encoding the one or more tumor polypeptides prior to the administration, and wherein the tumor exosomes are fragmented.

14. The method of claim 9, wherein the animal is a human.

15. A method of treating an animal with a tumor comprising:
   electroporating one or more dendritic cells with:
      one or more tumor exosomes,
      one or more tumor exosome lysates,
      amplified tumor RNA obtained from one or more tumor exosome lysates,
      tumor proteins isolated from the one or more tumor exosome lysates, or any combination thereof, and
   administering to the animal an effective amount of a composition comprising the one or more electroporated dendritic cells.

16. The method of claim 15, wherein the one or more dendritic cells are isolated from the animal.

17. The method of claim 15, wherein the one or more tumor exosomes are isolated from a biological sample of the animal.

18. The method of claim 17, wherein the biological sample is a blood sample, a urine sample or tumor ascites sample.

19. The method of claim 15, wherein the animal is a human.

* * * * *